United States Patent
Callede et al.

(10) Patent No.: US 9,848,854 B2
(45) Date of Patent: Dec. 26, 2017

(54) DEVICE FOR TAKING AT LEAST ONE SAMPLE OF TISSUE

(71) Applicant: COLOPLAST A/S, Humlebaek (DK)

(72) Inventors: David Callede, Sarlat la Caneda (FR); Laurent Pivard, Dortan (FR); Denis Pinaud, Draillant (FR); Fabrice Teppe, Oyonnax (FR); Adrien Moine, Evian (FR)

(73) Assignee: Coloplast A/S, Humlebaek (DK)

( * ) Notice: Subject to any disclaimer, the term of this patent is extended or adjusted under 35 U.S.C. 154(b) by 522 days.

(21) Appl. No.: 14/369,203

(22) PCT Filed: Jan. 11, 2013

(86) PCT No.: PCT/EP2013/050460
§ 371 (c)(1),
(2) Date: Jun. 27, 2014

(87) PCT Pub. No.: WO2013/107695
PCT Pub. Date: Jul. 25, 2013

(65) Prior Publication Data
US 2015/0005663 A1    Jan. 1, 2015

(30) Foreign Application Priority Data

Jan. 16, 2012   (EP) .................................... 12290014

(51) Int. Cl.
*A61B 10/02*     (2006.01)

(52) U.S. Cl.
CPC ...... *A61B 10/0266* (2013.01); *A61B 10/0275* (2013.01); *A61B 2010/0208* (2013.01)

(58) Field of Classification Search
CPC ............ A61B 10/0275; A61B 10/0208; A61B 2010/0208

(Continued)

(56) References Cited

U.S. PATENT DOCUMENTS

| | | |
|---|---|---|
| 5,842,999 A | 12/1998 | Jacobs |
| 7,153,274 B2 | 12/2006 | Stephens |
| 2004/0068231 A1* | 4/2004 | Blondeau ........... A61B 10/0275 604/157 |

FOREIGN PATENT DOCUMENTS

EP         0318447 A1    5/1989

* cited by examiner

*Primary Examiner* — Daniel Cerioni
*Assistant Examiner* — Yasmeen S Warsi
(74) *Attorney, Agent, or Firm* — Coloplast Corp., Coloplast A/S; Nick Baumann

(57) ABSTRACT

This invention relates to a device (10) for taking at least one sample of soft tissue from an organ, said device comprising a body (11) and a needle (12) formed by a stylet (13) and a cannula (14) coaxial with said stylet, said device comprising a mechanism for arming the needle, designed for sequentially moving the cannula (14) and then the stylet (13) from a rest position wherein the stylet and the cannula are extended towards the outside of the body, to a shooting position wherein the stylet and the cannula are retracted towards the rear of the body, and a triggering mechanism designed to release the stylet then the cannula and to allow their displacement from the shooting position to the rest position, the cannula being coupled kinematically to a cannula slider (24) comprising at least one retaining element (26) for maintaining the cannula slider in a shooting position, the stylet being coupled kinematically to a stylet slider (30) comprising at least one retaining element (32) for maintaining the stylet slider in a shooting position and means for unlocking (34) the cannula slider. At least one of said retaining elements of the cannula slider (26) or stylet slider (32) comprises at least a hook (50) arranged to rest against a corresponding retaining element (27, 33) in a locking position and to release the retaining element (27, 33) in a shooting position. The retaining element is unhooked (Continued)

from said retaining means by a striker (51), this striker comprising elastic blades (52) which number is at least equal to the number of hooks of said retaining element, these elastic blades (52) being arranged to be in contact with said hooks. The striker (51) cooperates with a stressing ring (53) arranged around the elastic blades (52) of the striker (51), this stressing ring (53) being arranged to be movable in a first stressing position, in which said ring acts on the elastic blades (52) of the striker and forces them in order to allow a sufficient force to be applied to the hooks (50) of the retaining element, and a second free position, in which said stressing ring (53) does not apply a sufficient stress to the hooks (50) for unhooking the hooks from the retaining means.

9 Claims, 4 Drawing Sheets

(58) Field of Classification Search
USPC .......................................................... 600/567
See application file for complete search history.

DEVICE FOR TAKING AT LEAST ONE SAMPLE OF TISSUE

TECHNICAL FIELD

The present invention relates to a device for taking at least one sample of soft tissue from an organ, said device comprising a body and a needle formed by a stylet and a cannula coaxial with said stylet, said device comprising a mechanism for arming the needle, designed for sequentially moving the cannula and then the stylet from a rest position wherein the stylet and the cannula are extended towards the outside of the body, to a shooting position wherein the stylet and the cannula are retracted towards the rear of the body, and a triggering mechanism designed to release the stylet then the cannula and to allow their displacement from the shooting position to the rest position, the cannula being coupled kinematically to a cannula slider comprising at least one retaining element for maintaining the cannula slider in a shooting position, the stylet being coupled kinematically to a stylet slider comprising at least one retaining element for maintaining the stylet slider in a shooting position and means for unlocking the cannula slider.

BACKGROUND ART

Nowadays, there are several devices for taking samples of soft tissue, these devices being generally used to extract, in a minimally invasive way, a sample of an organ from a human or an animal for analysis purpose. This extraction operation is generally known as biopsy and the used device is known as a biopsy gun.

Such a sampling device comprises in particular a sampling needle formed by a cannula and a stylet, an arming mechanism placed on a body and a trigger also placed on the body of the device.

The arming mechanism is used to partially retract the needle towards the inside of the body of the device, the device is placed near the organ from which one wishes to take a sample, then the trigger is pressed so that the needle can penetrate into the organ. The needle being formed by a stylet and by a cannula, the stylet penetrates into the organ, the cannula then covers the stylet. This stylet comprises at least one notch receiving the tissue to be taken. When the cannula covers the stylet, the tissue sample is trapped in the notch and is cut. The unit is withdrawn so that the sample(s) arranged between the stylet and the cannula can be taken. An example of application of such a device is taking tissues of the prostate.

The arming of the needle is generally achieved in two phases, namely the arming of the cannula in a first phase and the arming of the stylet in a second phase.

During sampling of tissues, it is frequent that the person who carries out the sampling has only one free hand, the other hand being used to hold other medical devices such as for instance an echographic probe. In this case, it is important to be able to manipulate the sampling device with one single hand. The manipulation implies here the arming of the cannula, the arming of the stylet and the release of the shot allowing for the sample to be taken.

One of the existing devices, which enable a manipulation with one single hand, is described in the U.S. Pat. No. 7,153,275. This device is perfectly functional if it is manipulated in a correct way i.e. in most cases. However, it happens that certain bad manipulations cause problems. In particular when the arming of the cannula or of the stylet has not been achieved correctly, the shot can be released in an unintentional way. This can cause problems because a shot can be released in particular before the device is correctly placed near the organ of which one wishes to take a sample.

Another problem that has been encountered with this kind of device is due to the fact that in case of incorrect manipulation the arming mechanism and the shooting mechanism may become totally jammed, thus rendering the device unusable.

This invention proposes to realize a tissue sampling device which has the advantages of the devices of the prior art i.e. it is possible to use this device with one hand. However, this device does not have the drawbacks of the systems of the prior art. Thus, even in case of bad manipulation, the shot is not released in an unintentional way. Moreover, the device cannot be jammed as a result of a bad manipulation.

Furthermore, and especially in implementations of the invention wherein the sampling device may be a single-use sampling device, particularly the risk of jamming of the needle and/or the cannula individually or in relation to each other is reduced or eliminated. This is at least partly because the sampling device, and particularly the movable parts thereof e.g. the needle and the cannula, is then assembled correctly during manufacture leaving no risks of a user putting the parts together in the wrong manner as could very well be the case with re-useable sampling devices. In addition, a single-use device is also significantly less prone to risks of contamination, e.g. by bacteria on a user's hands.

Moreover, as a single-use sampling device may enable production tolerances different from those of a re-useable sampling device, it is in most cases less costly to manufacture than such re-useable sampling devices. Thereby, the improved security mechanisms against unintentional firing of the sampling device according to the different implementations of the invention may be particularly, but not exclusively, suitable for single-use sampling devices in order to meet any potential risks due to such different production tolerances as mentioned above.

DISCLOSURE OF THE INVENTION

The aim of the invention is reached by a sampling device as defined in the preamble and characterized in that at least one of said retaining elements of the cannula slider or of the stylet slider comprises at least one hook arranged to rest against a corresponding retaining element in a locking position and to be released from the retaining element in a shooting position, said retaining element is unhooked from said retaining means by a striker, this striker comprising elastic blades which number is at least equal to the number of hooks of said retaining element, these elastic blades being arranged in order to be in contact with said hooks, the striker cooperates with a stressing ring placed around the elastic blades of the striker, this stressing ring being arranged to be movable in a first stressing position, in which said ring acts on the elastic blades of the striker and forces them in order to allow a sufficient force to be applied to the hooks of the retaining element, and a second free position, in which said stressing ring does not apply a stress to the hooks sufficient to unhook the hooks from the retaining means.

According to the present invention, the device for taking samples comprises a cannula slider integral with the cannula and a stylet slider integral with the stylet.

These sliders comprise retaining means enabling the sliders to be maintained in a position such that the stylet and/or the cannula are armed i.e. they are in a position ready for a sampling shot. The device of the invention further comprises means allowing the release of the cannula slider and of the stylet sliders in order to carry out a shot. According to the invention, prior to the full arming, the means enabling the release of the sliders do not have access to the corresponding slider i.e. they cannot release the sliders. Once the arming of the device has been totally and properly carried out, the means enabling the release of the sliders can have access to the corresponding slider and a sampling shot can be triggered.

The device of the invention allows avoiding the unintentional triggering of a shot. Such an unintentional shot can occur in the devices of the prior art in particular when the arming of the cannula has not been made correctly.

In the present invention, the biopsy gun can comprise two security systems. One of them prevents the involuntary displacement of the trigger releasing a shot. The other prevents an unintentional shot due to the wrong arming. For this scope, the mechanism for arming the cannula cooperates with a security mechanism. This cooperation provides a guarantee that if the security mechanism is not activated, the arming is not achieved. If the security mechanism is activated, an unintentional shot cannot occur. Thanks to this, there is no risk that a shot is released accidentally.

By virtue of the geometry of the device, the propulsion and retaining elements for the stylet and the cannula are arranged symmetrically around a longitudinal axis materialized by the stylet. This ensures that there are few transversal forces. Such transversal forces have the effect of increasing the friction between the parts, of causing wear and of risks of rupture as well as of jamming. By suppressing these transversal forces, it is possible to use smaller springs as it is no longer necessary to fight against friction. The biopsy gun is thus easier to use since the arming is made easier. Moreover, the gun can be used more often since the jamming risk is reduced.

Having symmetrical retaining elements for the stylet and the cannula ensures a greater security since at least two elements retain the stylet and the cannula. Moreover, in case of an asymmetrical retaining element, a force can act on the retaining element and possibly deform it and/or unhook it. This can lead to jamming, ruptures or an unintentional shot.

BRIEF DESCRIPTION OF THE DRAWINGS

The present invention and its advantages will be better understood with reference to the enclosed drawings and to the detailed description of a particular embodiment, in which.

BEST MODE FOR CARRYING OUT THE INVENTION

Figure 1:
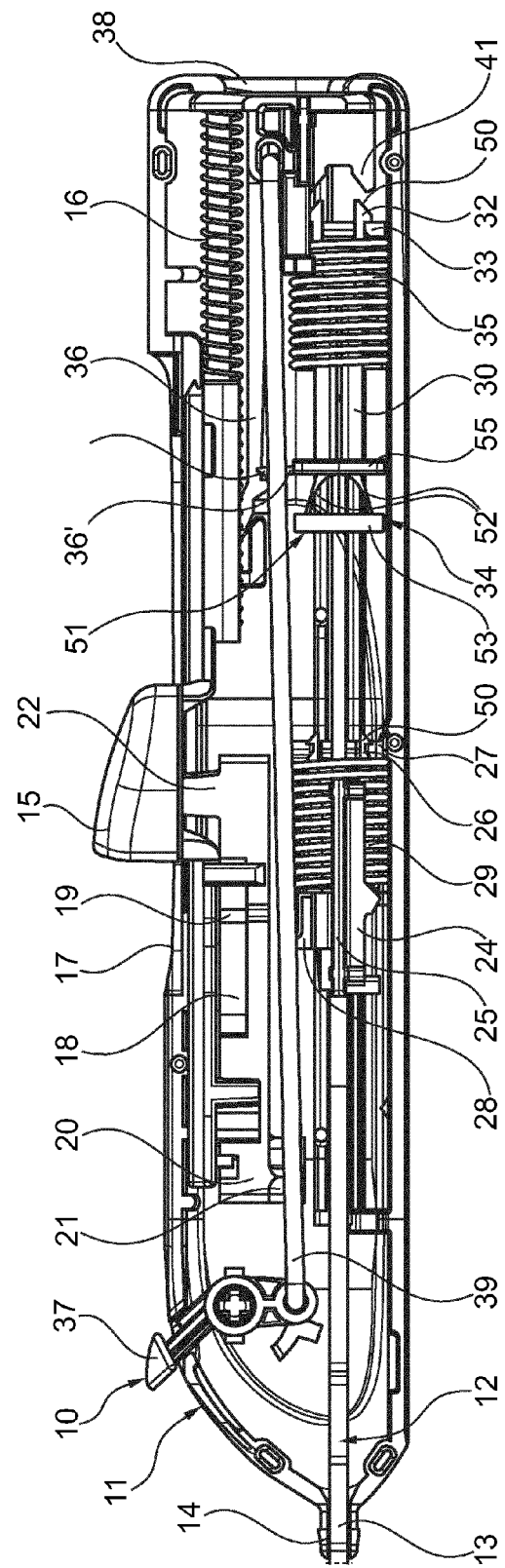
FIG. 1 is an overview of the device of the invention.

With reference to the drawings and in particular to FIG. 1, the sampling device 10 according to this invention essentially comprises a body 11 and a needle 12. The needle is formed by a stylet 13 and by a cannula 14. The stylet comprises a tip allowing a penetration of the needle into the organ from which one wishes to take a sample. Furthermore, this stylet comprises at least one notch (not represented). In practice, the stylet 13 comprises a relatively long notch that enables a sample of great length to be taken. The cannula 14 slides around the stylet 13 and is used on one hand to section the tissue into which the stylet has penetrated and on the other hand to keep in place the tissues taken at the time of the extraction of the needle from the organ.

The body 11 essentially comprises an arming mechanism arranged to arm the needle 12 and a triggering device arranged to release a shot of the needle for the intended sampling. More particularly, the arming of the needle is carried out in two phases, namely a phase of arming the cannula 14 and a phase of arming the stylet 13.

The sampling is made by a shot of the needle. Such a shooting also comprises two phases, namely a displacement phase of the stylet 13 under the effect of a propelling power of the stylet, then a displacement phase of the cannula 14 under the effect of a propelling power of the cannula. Releasing a shot is achieved by liberating the displacement of the stylet. The displacement of the cannula is a consequence of the release of the stylet as it will be explained in detail below.

In practice, the mechanism for arming the cannula and the mechanism for arming the stylet use only one arming button 15 which acts differently depending on whether the arming of the cannula has already been carried out or not. This arming button cooperates with a return spring 16 of the arming button, this spring having the function to bring back the arming button 15 to the rest position i.e. towards the front of the body, when it is not manipulated.

The body of the device is formed by two parts which, once assembled, comprise guidance grooves intended to ensure the displacement of the parts. The body also comprises a slit 17 in which the arming button moves.

With reference to the figures, the arming button 15 cooperates with a platform 18. This platform can pivot around a platform axis 19 integral with the arming button. One of the ends of the platform, located near the front end of the sampling device i.e. the needle-end of the sampling device, comprises a widened zone 20, each end of this widened zone including a finger 21 whose function is described in detail below. The rear end of the platform comprises a pushing device 22 whose function is also described in detail below.

The platform 18 is connected to the arming button 15 by the platform axis 19 and by a return device (not represented) that can be in particular a spring or an elastic tab and which has the function of keeping this platform in a predefined position called a rest position.

The mechanism for arming the cannula 14 is intended to move the cannula into the shooting position. This cannula is coupled to a cannula slider 24. According to one advantageous embodiment, the cannula slider 24 comprises two fins 25 disposed in a plane containing also the cannula. These two fins 25 cooperate with two guide grooves realized in the body of the device so as to ensure an effective sliding motion of the cannula slider 24. This slider comprises, at its rear end, a retaining element 26 of the cannula slider. According to an advantageous embodiment, the retaining element is formed by two hooks 50. Advantageously, these hooks are symmetrical and realized so as to have a certain flexibility, which allows for them to be hooked onto a retaining device 27 of the cannula slider and to be unhooked from this device by bringing the hooks together. It is also possible to use only one hook or several hooks arranged asymmetrically.

Furthermore, the cannula slider 24 comprises a spur 28 cooperating with one of the fingers 21 of the platform. The cannula slider cooperates with a spring 29 for the propulsion of the cannula slider, which is arranged between the cannula slider 24 and the retaining device 27 of the cannula slider.

This spring 29 is designed to supply the required force to propel the cannula slider towards the front of the body. The displacement of the cannula slider towards the back of the body provokes the compression of this spring.

The mechanism for arming the stylet is intended for the displacement of the stylet into the shooting position, this displacement being achieved after the cannula 14 has been armed. To that effect, the stylet 13 is coupled to a stylet slider 30, which comprises a spur 31 near its front end and a retaining element 32 at its rear end. Like for the cannula slider, the retaining element 32 can be formed by two partially elastic hooks 50. It can also be formed only by one hook or by several hooks arranged symmetrically or asymmetrically.

This retaining element 32 can be hooked on a retaining device 33 of the stylet slider and can be unhooked from this device by approaching the hooks to each other.

Like for the cannula slider, the hooks of the stylet slider are sufficiently flexible to be able to be deformed one towards the other and sufficiently rigid to be able to be maintained on an adequate support.

The stylet slider 30 comprises, at its front end i.e. at the side of the cannula slider 24, means for unlocking 34 the cannula slider These unlocking means 34 are illustrated with more details in FIGS. 2 to 8. They comprise a striker 51 formed by elastic blades 52 arranged so that they can face the hooks 50 of the retaining elements 26. These unlocking means 34 further comprise a stressing ring 53. The elastic blades 52 are such that when no stress is applied to them they are unable to release the hooks 50 from the corresponding retaining device. This result can be achieved in two different ways. In a first way, in the absence of stresses, the elastic blades 52 are at a sufficient distance from one another so that they do not enter into contact with the hooks 50. Only stresses applied to the elastic blades 52 allow them to be brought close together in such a way that they can enter into contact with said hooks.

In a second way, the elastic blades 52 can enter into contact with the hooks 50, but their elasticity is such that in the absence of stress, these elastic blades are not able to apply a force sufficient to release the hooks 50 from the retaining device to which they are attached. As mentioned above, only a stress on the elastic blades allows these elastic blades to release the hooks 50.

The elastic blades form part of a single element. The maximum width of this part in the absence of stress, or in other words, the maximum spacing between the elastic blades, corresponding to the front side of this part, is higher than the width of the rear side of this part i.e. in the area wherein the elastic blades are linked to each other. A shape similar to a cross-sectional truncated cone is well suited for this part. This piece is integral with the stylet slider.

As shown in the figures, the stressing ring 53 is placed around the elastic blades 52 of the striker 50.

The relative size of the stressing ring 53, of the hooks 50 and of the striker 51 is such that when the stressing ring is placed towards the front of the striker 51 i.e. on the side of the hooks 50, the elastic blades 52 are forced to move toward one another. In this configuration, the elastic blades 52 are located in order to be able to rest against the hooks and to apply a force sufficient to unhook the hooks from one another and thus for releasing them from the retaining device 27.

On the contrary, when the stressing ring 53 is located towards the rear of the device, the elastic blades 52 are free and are not able to move the hooks 50 and to release them from the retaining device.

The retaining device 27 comprises slits 54 in which the elastic blades 52 can penetrate. The detailed operation of the invention is described with more details below. Therefore, the width of the slits must be more than the thickness of the elastic blades 52. As it should be easily understood, the width of the hooks 50 must be greater than the width of the slits 54.

The stylet slider 30 cooperates with a spring 35 for the propulsion of the stylet slider, which is placed between the stylet slider 30 and the retaining device 33 of the stylet slider. This spring is designed to supply the required force to propel the stylet slider 30 towards the front of the body. The displacement of the stylet slider towards the back of the body provokes the compression of this spring.

A rear stop 55 made in the housing is placed near the stylet slider. Its function is described in detail below.

The device of the invention further comprises a security element 36 which can advantageously be formed by a security hook cooperating with a rear shoulder 36' of the stylet slider and with the spur 31 of this slider.

The device according to this invention further comprises a triggering device. According to an advantageous embodiment, this triggering device comprises two triggers 37, 38 connected together by a rod 39. One of the triggers 37 is placed in the front of the body, in front of the arming button 15 and the other trigger 38 is placed in the rear of the body. The rear trigger 38 is associated with a return spring of the trigger, designed to bring the trigger back in the original position after it has been pressed. This enables the user to easily access the triggering mechanism, whatever the position of the hand when using the device.

The rear trigger 38 comprises means for unlocking 41 the stylet slider formed by two elements arranged in inclined planes.

Figure 4:
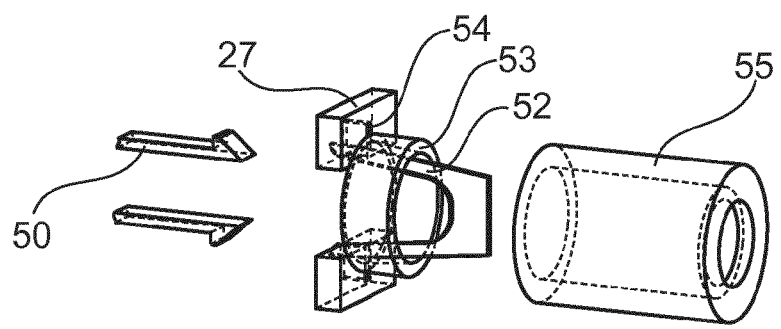
Figure 8:
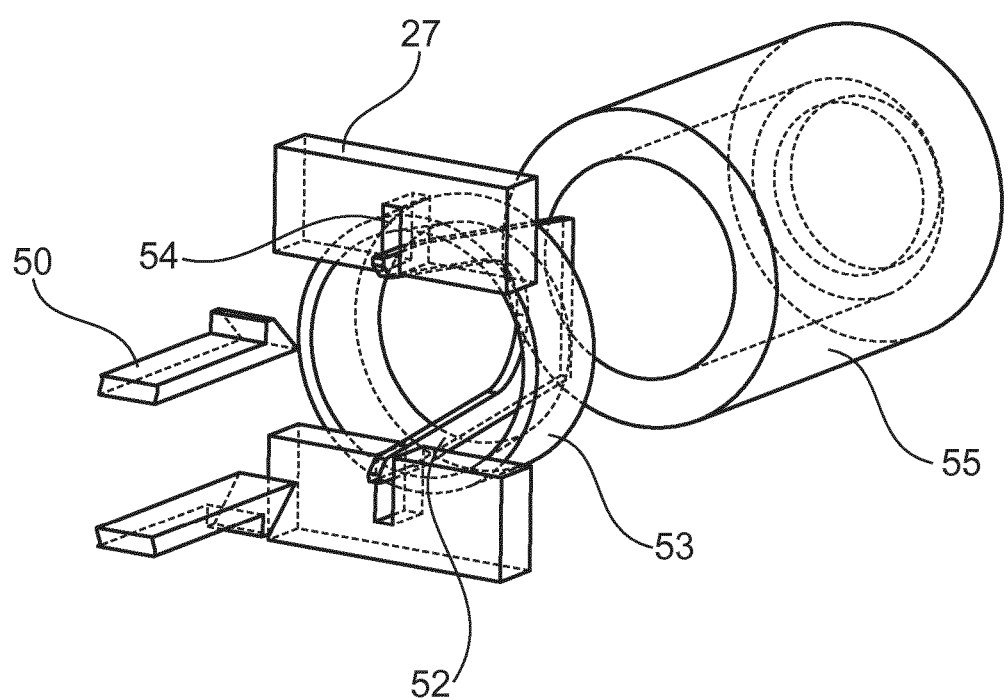

The sampling device according to this invention operates in the following way. Let us suppose that the initial position is a position in which the cannula 14 and the stylet 13 are maximally extended towards the outside of the body 11 of the device. This position corresponds to the normal position of the device when it is not going to be used, i.e. rest position. This position is shown in FIG. 1. In this position, the striker 50 has a configuration such as shown in FIGS. 4 and 8.

In a first phase, the arming of the cannula 14 is carried out. During this operation, the user actuates the arming button 15, making it slide towards the back of the device 10. The platform 18 being integral with the arming button 15, the displacement of the latter also draws the platform backwards. One of the fingers 21 of the platform 18 comes in contact with the spur 28 placed towards the front end of the cannula slider 24. The latter is thus displaced backwards, in opposition to the force of the spring 29 for the propulsion of the cannula slider. This movement is carried out until the retaining elements 26 of the cannula slider 24 enter into contact with the retaining device 27 of the cannula slider. This retaining device 27 is for instance a ring realized in the body of the device. The ring comprises a central hole in which the ends of the hooks 50 of the cannula slider pass. These hooks lean on the back face of the ring and maintain the cannula slider 24 in opposition to the force of the propulsion spring of this cannula slider.

At the end of the stroke of the platform i.e. just before the retaining elements 26 of the cannula slider are maintained by the corresponding retaining device 27, the platform 18 comes in contact with the spur 31 of the stylet slider and displaces the latter slightly backwards. Following this displacement, the hook forming the security element 36 cooperates with the rear shoulder 36' of the stylet slider and retains this slider in this position by preventing it from moving forward.

The end of the stroke of the platform also has the effect of displacing the cannula slider 24 into a position such that the retaining element 26 of the cannula slider is maintained on the retaining device 27 of the cannula slider.

When the stylet slider 30 is retained by the security hook, the unlocking means 34 being part of the stylet slider 30 or in other words, the means for unlocking the cannula slider, cannot move sufficiently forward to separate the hooks of the cannula slider from the retaining organs 27 of these hooks. In this way, if the arming of the cannula is not carried out until the end, the hooks of the cannula slider do not hook to the corresponding retaining device, which is immediately detected by the user who simply needs to restart the arming of this cannula. If the arming of the cannula has been carried out correctly, the hooks of the retaining device are maintained in place and the hook of the security element 36 cooperates with the stylet slider 30 so as to prevent from advancing beyond a predetermined position. In this way, an unintentional release of the shot is not possible.

Moreover, in this position, the stressing ring 53 does not apply any stress to the elastic blades 52. As a result, even if the striker enters into contact with the hooks 50, these will not be released from the retaining device.

When the arming of the cannula is terminated, the arming button 15 is released. It returns to its initial position towards the front of the device, under the effect of the return spring 16 of the arming button.

During the forward displacement of the platform 18, following the forward displacement of the arming button 15, a ramp of the platform comes into contact with a plug realized in the body. This ramp has the effect of rotating the platform 18 around the platform axis 19, against the force of the return device of the platform. It should be noted that according to the chosen practical realization, it is also possible to provide for the return device of the platform to be constrained before the arming of the cannula is terminated and to be liberated when the arming of the cannula is terminated.

For the arming of the stylet 13, the arming button 15 is displaced backwards again. However, the platform 18 is no longer in the initial position. Indeed, the latter has pivoted around the platform axis 19, as the ramp of the platform has been displaced by the support against the plug. By this rotation, the finger 21 of the platform does not, on one side, come into contact with the spur 28 of the cannula slider, and on the other side, the pushing device 22 of the platform leans against the spur 31 of the stylet slider. In a first phase, the pushing device 22 is placed next to the spur 31 while in a second phase, the pushing device 22 rests against the spur 31.

Figure 2:
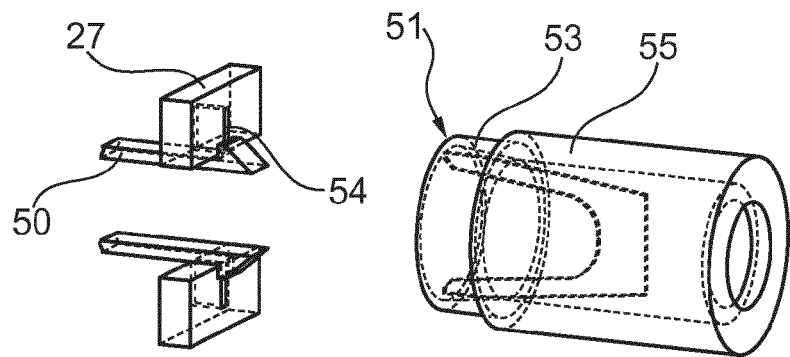
FIGS. 2 to 4 are side views of a detail of the device of the invention, in different positions.
Figure 5:
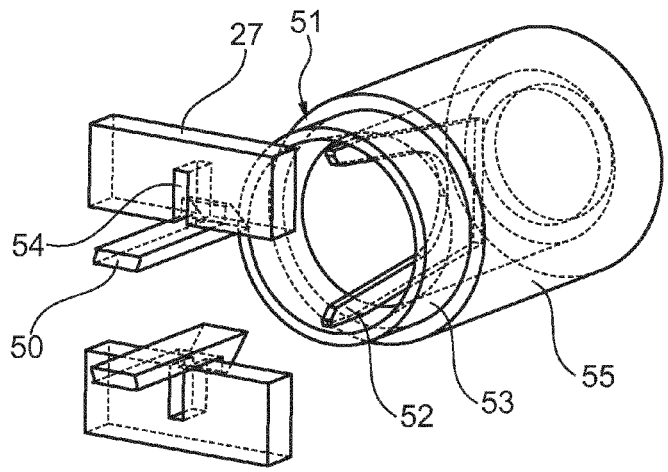
FIGS. 5 to 8 are front views of the device of the invention, of the detail shown in FIGS. 2 to 4, at different stages of use of such device.

The stylet slider is thus displaced towards the back of the device, in opposition to the force of the propulsion spring 35 of the stylet slider, until the retaining elements 32 of the stylet slider are placed in the retaining device 33 of the stylet slider. This retaining device is similar to the retaining device 27 of the hooks of the cannula slider. It has thus advantageously an annular form with a hole into which the hooks of the stylet slider fit. Since the elastic blades 52 are integral with the stylet slider 30, the displacement of this stylet slider towards the rear during the arming of the device will also move the elastic blades towards the rear. During this displacement, the stressing ring 53 rests against the rear stop 55, preventing said stressing ring 53 to exceed a certain limit position. This rear stop 55 is placed in such a way that, when the stylet slider is in armed position i.e. in a rearmost position, the stressing ring rests against the rear stop and is placed around the front end of the elastic blades 52. This stressing ring is held in position by the elasticity of the blades. The position reached at this stage is shown in FIGS. 2 and 5.

At this stage, the device is triggered out and ready for the shot. The device is stable in the sense that the cannula and stylet slider hooks are maintained against the corresponding retaining elements. The hook of the security element 36 is no longer in contact with the rear shoulder 36' of the stylet slider. The arming button 15 is released and returns to its initial position under the effect of the return spring of the arming button. The platform 18 also returns to its initial position.

If the arming of the stylet is not carried out correctly and the hooks of the cannula slider are not well maintained on the corresponding retaining device, the stylet slider moves in direction of the cannula slider. The security element 36 cooperating with the rear shoulder 36' of the stylet slider prevents the unlocking means 34 connected to this stylet slider (or means for unlocking of the cannula slider) from interacting with the retaining element 26 of the cannula slider. Moreover, if the arming has not been properly carried out, the stressing ring 53 will not rest against the rear stop 55. Therefore this ring does not apply any stress to the elastic blades 52 which are thus not able to release the hooks 50 from the retaining device 27. Thus, even in case of bad manipulation during the arming of the stylet, an unintentional shot cannot be released.

When the needle is armed, the sampling is started by a shot. This shot can be started by means of one of the triggers 37, 38. According to an advantageous embodiment, a security mechanism is provided for preventing a shot during an involuntary manipulation of one of the triggers and in particular of the front trigger. Before the release of the shot, it is necessary to laterally displace this front trigger 37 in relation to the body 11 in order to remove the security function of the mechanism. After the shot, it is necessary to laterally re-displace the front trigger 37 in order to reactivate the security function. This security is manual in the sense that the user has the choice whether to activate the function by displacing the trigger.

To release the shot, it is necessary to press one of the triggers 37, 38, the front or the rear one. Actually, in the disclosed embodiment, the shot is always released by a displacement of the rear trigger 38. However, the front trigger and the rear trigger being linked by the rod 39, a pressure on the front trigger has as result to move the rear trigger forward under the pressure of the rod. Thus the mechanism can be used by pressing either the rear trigger or the front trigger.

When the rear trigger 38 is pressed, the unlocking means 41 being part of the rear trigger (or means for unlocking the stylet slider) comes into contact with the hooks of the stylet slider and displaces them towards each other. In this way, they are released from the retaining device 33 of the stylet slider. This slider 30 is propelled forward under the effect of the propulsion spring 35 of the stylet slider.

As the hook of the security element 36 is integral with the rear trigger 38, the fact of displacing this trigger forward also has the effect of displacing the security hook forward and upward. Thus the stylet slider 30 is no longer retained by this hook and can advance far enough so that the unlocking means 34 being part of this stylet slider, come into contact with the hooks 26 of the cannula slider 24.

Figure 3:
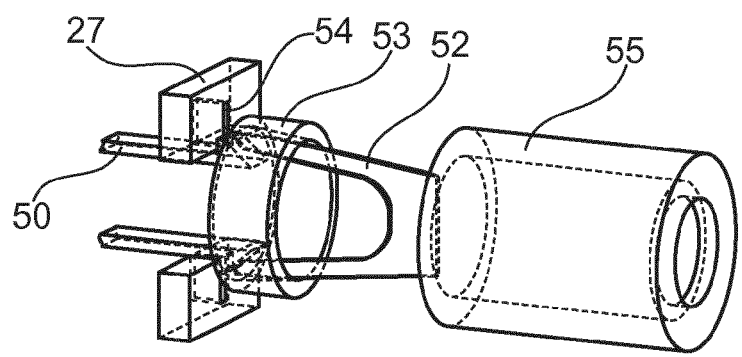
Figure 6:
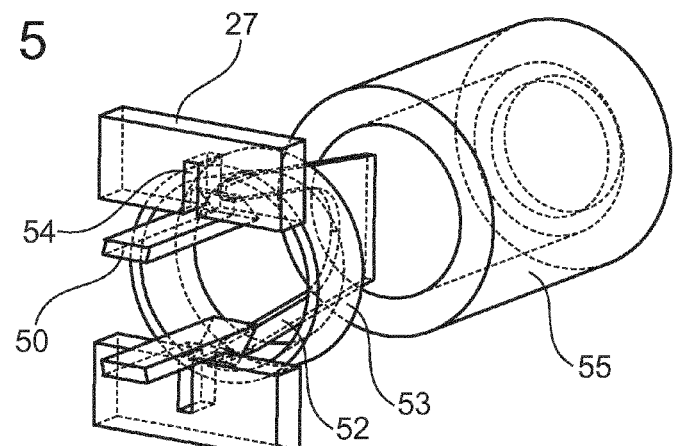

The means 34 for unlocking the cannula slider comes into contact with the hooks of the cannula slider, presses these hooks towards the centre and releases the retaining elements 27 of the cannula slider. More specifically, the stressing ring 53 is placed around the elastic blades 52 and applies a stress to the latter. Following the displacement of the stylet slider, the elastic blades 52 enter into contact with the hooks 50. Due to the form of the hooks and the elastic blades, such blades bring the hooks close together and release them from the retaining device. The position of the striker 51 is shown in FIGS. 3 and 6.

Figure 7:
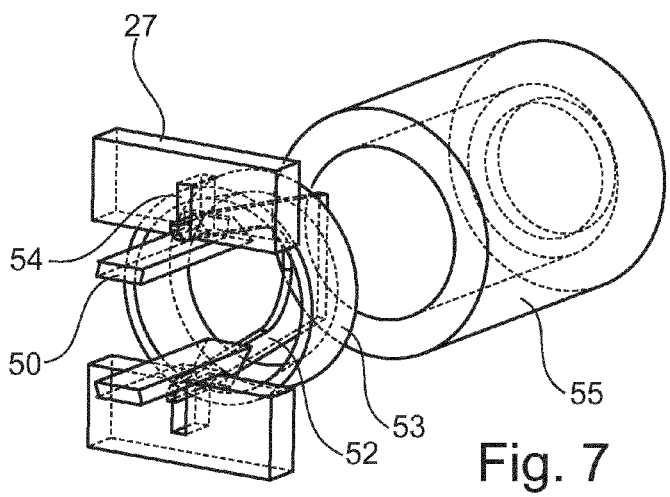

The elastic blades continue their stroke and penetrate into the slits 54. The retaining device 27 is used as front stop for the stressing ring 53. This position is shown in FIGS. 4, 7 and 8. As the elastic blades 52 penetrate into the slits 54 while the stressing ring 53 cannot exceed the retaining device 27, this ring is moved towards the rear of the piece carrying the elastic blades, in an area wherein the ring does not apply any stress to these blades.

The cannula slider 24 advances under the effect of the propulsion spring 29 of the cannula. This slider advances until it arrives at a stop realized in the body of the device. At this stage, the shot is terminated and the device can be withdrawn from the organ from which samples have been taken.

After the arming of the stylet, the platform 18 has returned to its rest position under the effect of the return device of the platform. After the shot, the pieces composing the device return to their initial positions. The sample taken is confined between the stylet 13 and the cannula 14, in the notch provided for this purpose. This sample can be withdrawn by moving back the cannula, for instance by carrying out an arming movement as previously explained. When the arming of the cannula is terminated, it is possible to withdraw the sample without any risk because an unintentional shot is not possible. If a new sampling has to be carried out, the arming button is operated so as to arm the device totally and to make it ready for the shot. If it is not necessary to take a new sample, the arming is carried out as well and a blank shot is made.

The present invention has several advantages in comparison with the devices of the prior art. In particular, by the setup of the retaining elements 26, 32 of the stylet and cannula sliders, it is possible to provide at least two symmetrical hooks. The forces applied on these hooks to hold them by the retaining means as well as during their unhooking during a shot are symmetrical. On one hand, this ensures that there is no flexing and/or twist on the needle and on the other hand, this enables a safer support of the hooks.

According to an advantageous realization, the needle is off-center towards the bottom of the device 10. This enables the use of the device in an easier way with another apparatus as for example an echographic probe.

In case of incomplete movement during the arming of the cannula, the hooks of the cannula slider are simply not maintained on the corresponding retaining device. This has the advantage that an unintentional shot is not possible and that the arming of the stylet is not possible if the arming of the cannula is not done correctly. If the arming of the stylet is not properly carried out, the elastic blades 52 cannot act on the hooks 50, thus also avoiding unintentional shots.

The device according to the invention can be operated by one single hand since the arming of the cannula and the arming of the stylet use the same arming button.

By the symmetrical construction of the retaining elements of cannula and stylet sliders and by the position of the propulsion springs of these sliders, the stresses are divided symmetrically around the axis of the needle. Thus, the risks of jamming between the stylet and the cannula are minimized, which in some implementations of the invention enables the use of the device several times and thus allows for a greater number of samples to be taken.

The reduction of the jamming risk allows for the reduction of the force of the propulsion springs while maintaining a high displacement speed for the sliders. This is advantageous for the user because a smaller force is necessary for arming the device. The manipulation with a single hand is easier in this way.

Using guide grooves realized in the body of the device and slider fins moving in these grooves also ensures an optimal guidance and a diminution of the jamming risk.

The invention claimed is:

1. A sampling device for taking a sample of soft tissue from an organ, the sampling device comprising:
a body and a needle oriented on a longitudinal axis of the body and of the sampling device, the needle formed by a stylet and a cannula coaxial with the stylet;
an arming button for arming the needle, the arming button connected to a platform provided with a platform finger and a platform pusher, the platform finger to engage a cannula slider of the cannula and adapted to move the cannula to a shooting position, the platform is rotatable on a platform axis to a rotated position that engages the platform pusher with a stylet slider of the stylet such that subsequent movement of the platform pusher moves the stylet to the shooting position, wherein the stylet and the cannula are retained in the shooting position with the stylet and the cannula retracted into the body of the sampling device;
at least one trigger adapted to release the stylet and the cannula from the shooting position;
the cannula being coupled kinematically to the cannula slider, the cannula slider comprising a first retaining element for retaining the cannula slider in the shooting position and the stylet being coupled kinematically to the stylet slider, the stylet slider comprising a second retaining element for retaining the stylet slider in the shooting position;
wherein at least one of the first retaining element of the cannula slider and the second retaining element of the stylet slider comprises at least one hook arranged to rest against a corresponding retaining device in a locking position and for releasing the corresponding retaining device in a shooting position, the at least one hook unhooked from the corresponding retaining device by a striker, the striker comprising elastic blades which number is at least equal to the number of the at least one hook, the elastic blades being arranged to be put in contact with the at least one hook, the striker cooperates with a stressing ring placed around the elastic blades of the striker, the stressing ring is movable in a first stressing position into contact with the corresponding retaining device in which the stressing ring contacts the elastic blades of the striker to bias the elastic blades of the striker toward the at least one hook to provide sufficient force to unhook the at least one hook from the corresponding retaining device, and a second free position in which the stressing ring does not provide sufficient force to unhook the at least one hook from the corresponding retaining element.

2. The sampling device according to claim 1, wherein in the absence of stress applied by the stressing ring, the elastic blades of the striker are arranged in such a way that the elastic blades cannot enter into contact with the at least one hook.

3. The sampling device according to claim 1, wherein in the absence of stress applied by the stressing ring, the elastic blades have an elasticity such that the elastic blades cannot apply a force to the at least one hook sufficient to unhook the at least one hook from the corresponding retaining device.

4. The sampling device according to claim 1, wherein the sampling device comprises a rear stop against which the stressing ring rests so as to pass from the free position to the stressing position.

5. The sampling device according to claim 1, wherein the sampling device comprises a front stop against which the stressing ring rests so as to pass from the stressing position to the free position.

6. The sampling device according to claim 5, wherein the front stop is formed by the corresponding retaining device.

7. The sampling device according to claim 1, wherein the corresponding retaining device comprises slits arranged in order to allow the passage of at least one area of the elastic blades of the striker.

8. A sampling device for taking a sample of soft tissue from an organ, the sampling device comprising:
   a needle formed by a stylet and a cannula coaxial with the stylet;
   an arming button connected to a platform, the platform configured to engage a cannula slider of the cannula and adapted to move the cannula to a shooting position and to engage a stylet slider of the stylet and adapted to move the stylet to the shooting position, the cannula slider comprising a cannula retaining element for retaining the cannula slider in the shooting position and the stylet slider comprising a stylet retaining element for retaining the stylet slider in the shooting position; and
   at least one trigger adapted to release the stylet and the cannula from the shooting position;
   wherein at least one of the cannula retaining element and the stylet retaining element comprises at least one hook arranged to rest against a corresponding retaining device in a locking position and for releasing the corresponding retaining device in a shooting position, the at least one hook configured to be unhooked from the corresponding retaining device by a striker comprising one or more elastic blades arranged to be put in contact with the at least one hook and a stressing ring placed around the elastic blades, where the stressing ring is movable to a first stressing position in which the stressing ring contacts the elastic blades of the striker to bias the elastic blades of the striker toward the at least one hook to provide sufficient force to unhook the at least one hook from the corresponding retaining device and a second free position in which the stressing ring is unable to bias the elastic blades to provide sufficient force to unhook the at least one hook from the corresponding retaining element.

9. A tissue sampling device comprising:
   a needle formed by a cannula coaxial with a stylet;
   an arming button connected to a platform, the platform configured to engage a cannula slider of the cannula and adapted to move the cannula to a shooting position and to engage a stylet slider of the stylet and adapted to move the stylet to the shooting position, the cannula slider comprising a cannula retaining element for retaining the cannula slider in the shooting position and the stylet slider comprising a stylet retaining element for retaining the stylet slider in the shooting position; and
   a trigger adapted to release the stylet from the shooting position and adapted to release the cannula from the shooting position;
   wherein at least one of the cannula retaining element and the stylet retaining element comprises a hook arranged to engage a corresponding one of the cannula retaining element and the stylet retaining element in a locking position;
   a striker comprising a blade and a stressing ring placed around a perimeter of the blade;
   wherein the stressing ring is movable to a first biased position in which the stressing ring biases the blade into contact with the hook to disengage the hook from the corresponding one of the cannula retaining element and the stylet retaining element;
   wherein the stressing ring is movable to a second non-biased position in which the stressing ring does not bias the blade, thus leaving the hook engaged with the corresponding one of the cannula retaining element and the stylet retaining element in the locking position.

* * * * *